(12) United States Patent
Huang et al.

(10) Patent No.: US 10,576,607 B2
(45) Date of Patent: Mar. 3, 2020

(54) METHOD FOR MICROBIALLY DRESSING A SUPER ABRASIVE TOOL

(71) Applicant: HUAQIAO UNIVERSITY, Quanzhou (CN)

(72) Inventors: Hui Huang, Quanzhou (CN); Fei Ma, Quanzhou (CN); Xipeng Xu, Quanzhou (CN)

(73) Assignee: HUAQIAO UNIVERSITY, Quanzhou (CN)

( * ) Notice: Subject to any disclaimer, the term of this patent is extended or adjusted under 35 U.S.C. 154(b) by 448 days.

(21) Appl. No.: 15/479,891

(22) Filed: Apr. 5, 2017

(65) Prior Publication Data

US 2017/0341203 A1    Nov. 30, 2017

(30) Foreign Application Priority Data

May 27, 2016   (CN) .......................... 2016 1 0365437

(51) Int. Cl.
   *B24B 53/00* (2006.01)
   *B24B 53/02* (2012.01)
   (Continued)

(52) U.S. Cl.
   CPC .............. *B24B 53/00* (2013.01); *B24B 49/12* (2013.01); *B24B 53/02* (2013.01); *B24B 53/04* (2013.01);
   (Continued)

(58) Field of Classification Search
   None
   See application file for complete search history.

(56) References Cited

U.S. PATENT DOCUMENTS 3,843,464 A * 10/1974 Usami et al. ............. B08B 7/00
                                                    435/264
4,822,413 A *  4/1989 Pooley ..................... C22B 3/08
                                                    423/27
(Continued)

FOREIGN PATENT DOCUMENTS

CN       1231329 A     10/1999
CN       1522292 A      8/2004
(Continued)

OTHER PUBLICATIONS

Valdes J., Pedroso I., Quatrini R., Dodson R. Tettelin H., Blake II R., Eisen J., Holmes D., Acidithiobacillus ferrooxidans metabolism : from genome sequence to industrial applications, Nov. 12, 2008, BMC Genomics, 9:597 (Year: 2008).*

(Continued)

*Primary Examiner* — Joseph J Hail
*Assistant Examiner* — J Stephen Taylor
(74) *Attorney, Agent, or Firm* — Cooper Legal Group, LLC

(57) ABSTRACT

A microbial dressing method for super abrasive tools includes a kind of microbe which is capable of consuming the bond in a certain manner is selected to perform the microbial dressing. Specifically, the microbe is inoculated and cultured in the culture medium to a certain concentration, then the dressing area of the abrasive tool is immersed into the culture liquid to remove the bond in the surface by the action of the microbe, and the control of the dressing amount is realized by controlling the microbe concentration and the soaking time. Precise dressing for super abrasive products, particularly for fine grained abrasive tools can be realized using the present method.

10 Claims, 2 Drawing Sheets

(51) Int. Cl.
  *B24B 49/12* (2006.01)
  *B24B 53/04* (2012.01)
  *B24D 3/06* (2006.01)
  *C12N 1/20* (2006.01)
  *G01N 21/78* (2006.01)

(52) U.S. Cl.
  CPC ............... *B24D 3/06* (2013.01); *C12N 1/20* (2013.01); *G01N 21/78* (2013.01)

(56) References Cited

U.S. PATENT DOCUMENTS

| | | | | |
|---|---|---|---|---|
| 5,030,425 | A * | 7/1991 | Bowers-Irons | C12N 15/52 423/109 |
| 6,329,289 | B1 * | 12/2001 | Kimura | H01L 21/32115 257/E21.303 |
| 6,672,945 | B1 * | 1/2004 | Matsuo | B24B 49/14 451/41 |
| 2002/0173228 | A1 * | 11/2002 | Gunjima | B23K 26/032 451/5 |
| 2016/0138128 | A1 * | 5/2016 | Nicolay | C22B 3/18 435/262 |

FOREIGN PATENT DOCUMENTS

| | | |
|---|---|---|
| CN | 1568244 A | 1/2005 |
| CN | 200981197 Y | 11/2007 |
| DE | 19532802 C1 | 5/1997 |
| EP | 0322721 B1 | 10/1993 |

OTHER PUBLICATIONS

Chang J.H., Hocheng H., Chang H.Y., Shih A., Metal removal rate of Thiobacillus thiooxidans without pre-secreted metabolite, 2008, Journal of Materials Processing Technology, 20I (2008), 560-564 (Year: 2008).*

Yang T., Xu Z., Wen J., Yang L., Factors influencing bioleaching copper from waste printed circuit boards by Acidithiobacillus ferrooxidans, Jun. 1, 2009, Hydrometallurgy, 97 (2009), 29-32 (Year: 2009).*

Zhang D., Li Y., Possibility of biological micromachining used for metal removal, Apr. 1998, Science in China (Series C), vol. 41 No. 2, 151-156 (Year: 1998).*

* cited by examiner

METHOD FOR MICROBIALLY DRESSING A SUPER ABRASIVE TOOL

FIELD OF THE INVENTION

The present invention relates to abrasive dressing technique, and especially to a microbial dressing method for super abrasive tools.

BACKGROUND OF THE INVENTION

Abrasive dressing is a working process of shaping of the grinding tool via trimming or removing the dull surface of the grinding tool in order to restore the grinding performance of the working face and correct the geometrical shape. The effects of abrasive dressing mainly include two aspects: (1) to ensure that the grinding tool obtain the geometrical shape (also called truing); (2) to ensure that the abrasive grains on the surface of the grinding tool could have a certain exposure height (also known as sharpening). Dressing of the grinding tool in a timely and correct way is an indispensable procedure to improve the grinding efficiency and guarantee the grinding quality. For ordinary abrasive tools, diamond tools such as single-point diamond dresser and diamond wheel are used to complete the process of truing as well as sharpening simultaneously.

Super abrasive tools are grinding tools of which superhard abrasive (diamond and cubic boron carbide) are bonded by different kinds of bond. For super abrasive tools, since abrasive grains are of high hardness and the effective working layer is limited, truing and sharpening is done separately during abrasive dressing. Dressing of super abrasive tools is the key to ensure the normal use, which therefore has always been a hot research topic in this field.

At present, dressing of super abrasive tools includes the following two categories: (1) mechanical removal such as diamond dressing, wheel grinding, free-abrasive lapping, crush dressing, soft-elastic dressing, etc. to remove the bond and abrasive grains of super abrasive products via mechanical action between dressing tools and abrasive tools essentially; (2) dressing using other kinds of energy such as laser dressing which employing light energy to melt and remove the bond, EDM dressing which employing electro spark erosion to remove the bond, ultrasonic vibration dressing which employing ultrasonic energy to remove the bond, or new dressing method combining two methods described above. These kinds of dressing methods play good effect on ordinary super abrasive tools. However, there are still a lot of problems for above methods to be used in precision and ultra-precision grinding typed super abrasive tools.

Comparing with ordinary super abrasive tools, precision and ultra-precision grinding typed super abrasive tools is characterized by the use of fine grains with mostly micron or sub-micron scale, which bring a great challenge to dressing process. For the conventional mechanical removal method, it is difficult to control the removal amount of the bond in micron or sub-micron scale. So energy typed dressing methods are mainly used in fine grain super abrasive tools, including the following: spray sharpening, laser sharpening, MAP sharpening, ELID sharpening, etc. However, each method has a corresponding shortage: strict safety protection is necessary for spray sharpening; laser source using in laser sharpening is expensive, and also laser damage to diamond abrasive occur easily; MAP sharpening applies only to low rigidity abrasive tools; ELID sharpening requires a special DC supply unit which is expensive, and the current supply is unstable because of the wear of the brushes in the sharpening device, which affects the sharpening effect of the grinding wheel.

In order to achieve ideal dressing effect of fine grain super abrasive tools, a reasonable amount of bond removal must be guaranteed. If the removal amount is too large, abrasive grains are easy to fall off because of lacking holding force; if the removal amount is too small, it is difficult to achieve the dressing result because of not enough exposure height of grains and chip space. The removal amount controlling of ultra-precision grinding typed super abrasive tools is much more difficult since the size of grain is smaller, and therefore dressing of this type of abrasive tools is harder than ordinary abrasive tools. It is urgent to develop a novel dressing method which is cost-effective, energy-saving, environmental-friendly and suitable for ultra-precision grinding typed super abrasive tools.

SUMMARY OF THE INVENTION

The objective of present invention is to provide a microbial dressing method for super abrasive tools, which overcome the disadvantages of the existing technology.

The technical proposal of the present invention is that:

A microbial dressing method for super abrasive tools forming by combination of a super abrasive and a bond comprises the steps of:

1) selecting a microbe depending on the type of the bond, wherein the microbe is capable of consuming the bond in a certain manner;

2) culturing the selected microbe to obtain a microbial culture liquid with an appropriate cell concentration;

3) immersing the dressing surface of the super abrasive tool into the microbial culture liquid to remove the bond of the dressing surface by the action of the microbe;

4) determining the soaking time according to the required removal amount and the removal rate of bond material by the microbial culture liquid, observing the surface topography after the soaking time and judging whether to continue soaking until the requirement is reached, then taking out and cleaning the super abrasive tool.

In a preferred embodiment, the removal of the bond is realized through a circulation that the metabolite of the microbe reacts with the bond to consume the bond and produce a metabolic raw material and the metabolic raw material is reused by the microbe into the metabolite.

In a preferred embodiment, the reaction of the metabolite with the bond is oxidation-reduction reaction.

In a preferred embodiment, the microbe is *Acidithiobacillus ferrooxidans*, the metabolic raw material is $Fe^{2+}$ ion, the metabolite is $Fe^{3+}$ ion, and the bond is a metal-based bond which is capable of reducing $Fe^{3+}$ ion to $Fe^{2+}$ ion.

In a preferred embodiment, the bond is at least one kind of metal-based bond selected from the group consisting of copper-based, lead-based, zinc-based, cobalt-based, tin-based, chromium-based, cadmium-based, manganese-based, iron-based, nickel-based and aluminum-based bond.

In a preferred embodiment, in step 2, the *Acidithiobacillus ferrooxidans* is cultured in the culture medium until the concentration of $Fe^{3+}$ ion of the metabolite ranges from 6 g/L to 9 g/L to obtain the microbial culture liquid with the appropriate microbial concentration.

In a preferred embodiment, in step 3, the temperature of the microbial culture liquid is maintained at a range from 25° C. to 45° C.

In a preferred embodiment, the microbe is *Thiobacillus thiooxidans, Acidithiobacillus ferrooxidans, Acidithiobacillus caldus* or *Leptospirillum ferrooxidans*.

In a preferred embodiment, the super abrasive tool is rotated in the microbial culture liquid to immerse the dressing surface into the microbial culture liquid.

Comparing to the existing technology, the present invention has advantages as follows:

1. The microbial dressing method of present invention utilizes the microbe to remove part of the bond between the abrasive grains so that the abrasive grains protrude beyond the bond surface to form cutting edges, and gaps between the abrasive grains form certain chip space. The dressing tools of present invention are chemoautotroph microbes which are capable of utilizing the chemical energy released from the oxidation reaction of the bond to provide energy for their own growth and reproduction, and utilizing free carbon dioxide in the air as carbon source to satisfy their growth. Therefore, the biological removal method using microbes as tools does not need to provide any additional energy, which is a processing method conducive to resource sustainable development. The whole process seems like microbes "eat" the bond. On the other hand, the microbial dressing process does not produce carbon dioxide, but transform free carbon dioxide in the air into organics necessary to cell life of microbe such as glucides, proteins and lipids. The microbes using as dressing tools are isolated and domesticated from nature, which does not cause adverse effect to the ecological environment of the earth. However, other physical or chemical methods consume large amounts of mechanical, electrical or chemical energy during removal process. In addition, some of these methods utilize materials which are harmful to ecological environment and human health as dressing tools, such as: strong acid, alkali, etc. Some process may produce harmful gas or radiation such as radiation, strong light, toxic smoke, dust or poison gas, which increases the cost.

2. The microbial dressing method of present invention has very small surface or subsurface damage afterdressing, especially to the abrasive tool with very small abrasive grain size, the precision of microbial removal of the bond is high, and the holding force of the bond for the abrasive is improved, which cannot be achieved by some other methods at present. The process of microbial dressing is simple and requires only immerse the dressing surface into the microbial culture liquid, which is especially suitable for abrasive tools with large size. Unlike some traditional physical type of processing methods using cutting, fricting or other means, the abrasive tool substrate will not be squeezed or torn in microbial process; damage layer or heat affected zone will not be produced in the workpiece since no high temperature, neither residual stress occur in the workpiece. The tools of microbial dressing are microbes such as *Acidithiobacillus ferrooxidans* and *Thiobacillus thiooxidans* with small ceiling size, usually only about 0.5 micron in diameter, so the surface processing scale can be achieved in a micron or nano level. The lateral erosion is very small in microbial removal processing, generally only about half of the general chemical processing, which ensures the holding force of the bond for the abrasive while dressing is realized. Therefore, the present invention is a very promising new method for super abrasive tools dressing.

The present invention will be further described with the drawings and the embodiments.

DETAILED DESCRIPTION OF THE EMBODIMENTS

A microbial dressing method for super abrasive tools forming by combination of a super abrasive and a bond comprises the following steps:

1. selecting a microbe depending on the type of the bond, wherein the microbe is capable of consuming the bond in a certain manner;

2. selecting a particular culture medium, controlling appropriate environment conditions such as temperature, humidity and pH, and culturing the selected microbe to obtain a microbial culture liquid with an appropriate cell concentration;

3 immersing part or all of the super abrasive tool into the microbial culture liquid, or making the super abrasive tool move at a low speed according to the requirement of the dressing surface;

4. determining the soaking time according to the required removal amount and the removal rate of the bond material by microbial culture liquid, observing the surface topography after the soaking time and determining whether to stop soaking;

5. judging whether-it meet the requirement, soaking until the requirement is reached and then taking out and cleaning the super abrasive tool.

Specifically, the removal of the bond is realized in a way that the metabolite of the microbe reacts with the bond material to consume the bond and produce a metabolic raw material and the metabolic raw material is reused by the microbe to change into the metabolite. The microbe is *Acidithiobacillus ferrooxidans, Thiobacillus thiooxidans, Acidithiobacillus caldus, Leptospirillum ferrooxidans*, etc.

In a preferred embodiment, the reaction of the metabolite with the bond is oxidation-reduction reaction, and the solid-state bond is transformed to soluble product dissolving in the culture liquid through the reaction, thereby to achieve the removal of the bond.

In the following, the *Acidithiobacillus ferrooxidans* is used as an example of specific description.

Embodiment 1

Figure 1:
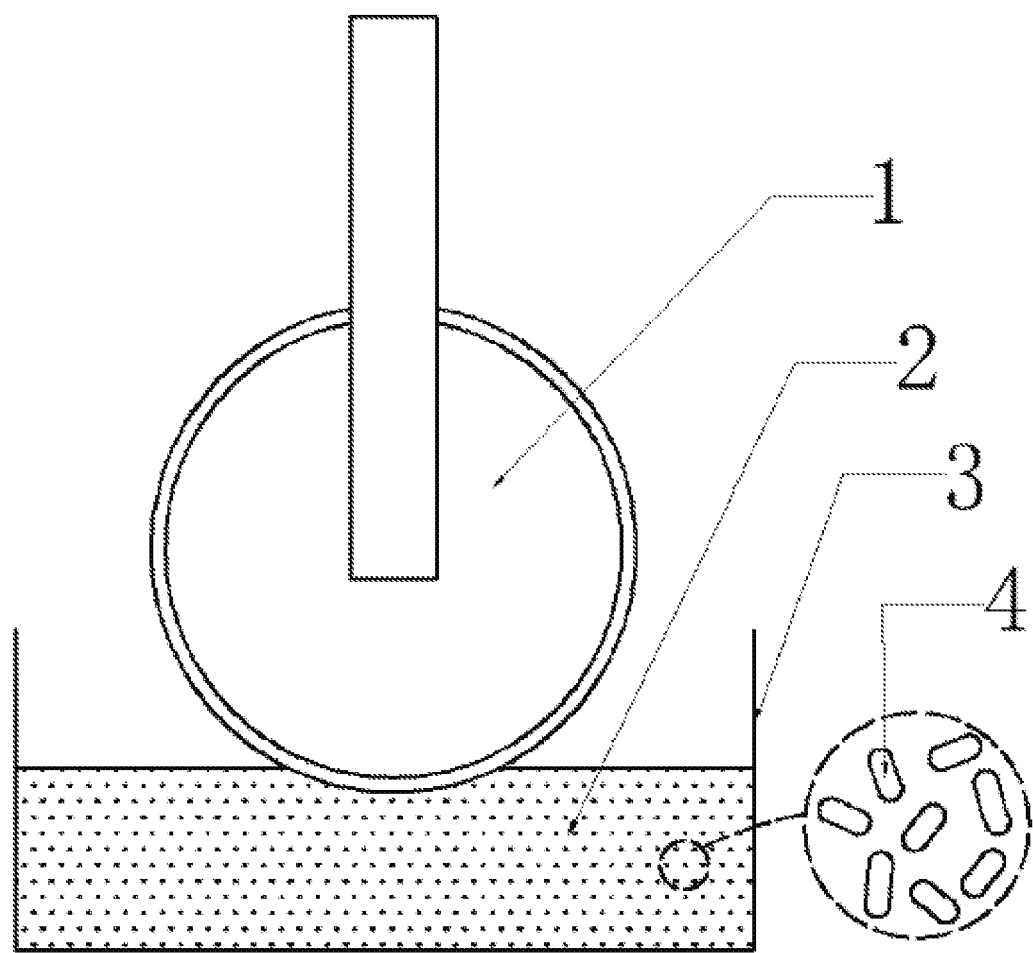
FIG. 1 illustrates structural representation of embodiment 1.

Referring to FIG. 1, grinding tool 1 of this embodiment is an iron-based bonded diamond grinding wheel with diamond abrasive grains in a size of about 20 μm. The selected microbe is *Acidithiobacillus ferrooxidans*. The dressing method is performed as follows:

a. A container 3 contains a volume of *Acidithiobacillus ferrooxidans* culture liquid 2 which is mainly composed of *Acidithiobacillus ferrooxidans* 4, culture medium and cell metabolites such as $Fe^{3+}$ ion. *Acidihiobacillus ferrooxidans* culture liquid 2 is obtained through inoculating and culturing in sterile culture medium. The culture medium is 9K medium and sterilized under high temperature, and then *Acidithiobacillus ferrooxidans* 4 is inoculated to the culture medium and cultured in a constant temperature shaker. *Acidihiobacillus ferrooxidans* 4 obtains sufficient nutrients and chemical energy from the culture medium to undertake cell division and proliferation. After the lag phase, the exponential growth phase, the plateau phase, the concentration of bacteria increases, light green $Fe^{2+}$ ions in the medium are continuously transformed into yellow $Fe^{3+}$ ions by *Acidithiobacillus ferrooxidans* 4 and the color of the culture liquid changes to yellow brown. The culture is stopped after the concentration of $Fe^{3+}$ ions reaches 8 g/L.

b. Container 3 is placed on the dresser table, the grinding machine is started to drive grinding tool 1 rotate at a low speed. The grinding area of grinding tool 1 is immersed in microbial culture liquid 2 and kept rotating. The temperature of *Acidithiobacillus ferrooxidans* culture liquid 2 is kept at a range from 30° C. to 40° C. $Fe^{2+}$ ions are changed to $Fe^{3+}$ ions continuously by series of self-biochemical reactions of *Acidithiobacillus ferrooxidans* 4. $Fe^{3+}$ ions are capable of reacting chemically with the iron-based bond because of the oxidability, and thereby the iron-based bond of zero-valence state is oxidized to $Fe^{2+}$ ions which are capable of dissolving into the culture liquid, meanwhile $Fe^{3+}$ ions are reduced to $Fe^{2+}$ ions. $Fe^{3+}$ ions are consumed continuously and reused by *Acidithiobacillus ferrooxidans* 4 to generate $Fe^{3+}$ ions, which forms a cycle process to realize the removal of the bond by the microbial culture liquid.

c. According to the abrasive grain size of grinding tool 1, the type of the bond and the removal rate of the bond material by the microbial culture liquid to the bond, the time of the iron-based grinding wheel soaking in the *Acidithiobacillus ferrooxidans* culture liquid 2 is calculated for about 36 minutes. The grinding area of the grinding wheel is maintained in the microbial culture liquid until the calculated soaking time is reached, then the surface topography is detected and the exposure height of the abrasive and the chip space between the abrasive is observed.

d. If the observation results do not meet the requirement, the dressing process is to be continued. If the observation results meet the requirement indicating that the removal amount of the bond is enough, then take out grinding tool 1 from the culture liquid and remove container 4, the dressing process is finished.

Embodiment 2

Figure 2:
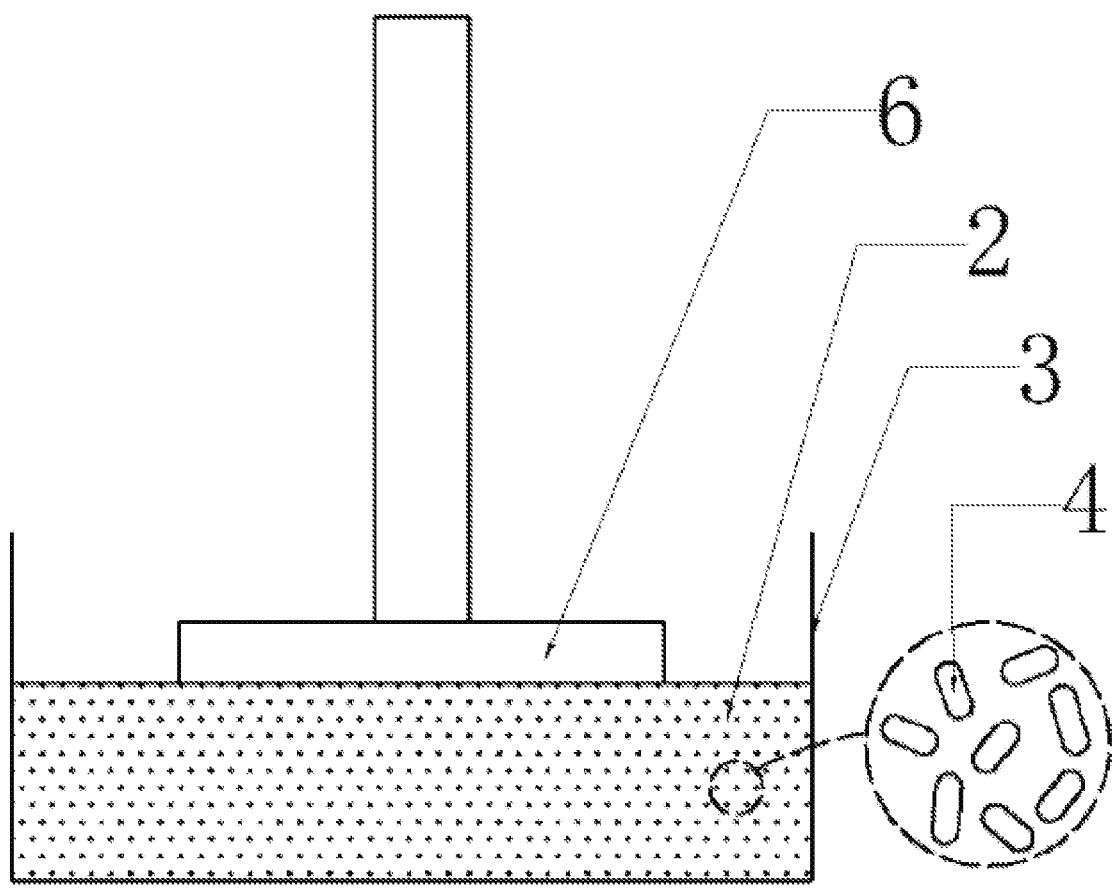
FIG. 2 illustrates structural representation of embodiment 2.

Referring to FIG. 2, grinding tool of this embodiment is a copper-based bonded diamond abrasive disk 6 with diamond abrasive grains in a size of about 10 μm. The selected microbe is *Acidithiobacillus ferrooxidans*.

The dressing method is similar to embodiment 1. Abrasive disk 6 is rotated at a low speed to immerse all the grinding area of abrasive disk 6 into *Acidithiobacillus ferrooxidans* culture liquid 2. $Fe^{3+}$ ions react chemically with the copper-based bond, and thereby copper-based bond of zero-valence state is oxidized to $Cu^{2+}$ ions which are capable of dissolving into the culture liquid to realize the removal of the copper-based bond. The time of abrasive disk 6 to be soaked in *Acidithiobacillus ferrooxidans* culture liquid 2 is calculated for about 15 minutes to achieve a certain removal amount of the bond, and then the dressing is finished.

Although the present invention has been described with reference to the preferred embodiments thereof for carrying out the patent for invention, it is apparent to those skilled in the art that a variety of modifications and changes may be made without departing from the scope of the patent for invention which is intended to be defined by the appended claims.

What is claimed is:

1. A method for microbially dressing a super abrasive tool comprising super abrasives and a binder, the method comprising:
   1) selecting microbes according to a type of the binder, wherein the microbes are configured to consume the binder;
   2) culturing the microbes to obtain a microbial culture liquid, wherein a concentration of $Fe^{3+}$ ions in the microbial culture liquid is in a range of 6 g/L to 9 g/L;
   3) immersing at least one surface of the super abrasive tool to be dressed into the microbial culture liquid to remove the binder from the at least one surface using the microbes; and
   4) determining an immersion time according to a preset removal amount and a removal rate of the binder using the microbes in the microbial culture liquid, observing a surface topography of the super abrasive tool after immersion of the at least one surface of the super abrasive tool for the immersion time, judging whether the preset removal amount has been achieved, and taking out and cleaning the super abrasive tool when the preset removal amount has been achieved.

2. The method for microbially dressing the super abrasive tool according to claim 1, wherein:
   the microbes are configured to consume the binder through metabolites of the microbes that react with the binder to consume the binder and produce metabolic raw materials, and
   the metabolic raw materials are reused by the microbes to form additional metabolites.

3. The method for microbially dressing the super abrasive tool according to claim 2, wherein a reaction between the metabolites and the binder comprises an oxidation-reduction reaction.

4. The method for microbially dressing the super abrasive tool according to claim 3, wherein:
   the microbes comprise *Acidithiobacillus ferrooxidans*,
   the metabolic raw materials comprise $Fe^{2+}$ ions,
   the metabolites comprise $Fe^{3+}$ ions, and
   the binder comprises a metal-based binder configured to reduce $Fe^{3+}$ ions to $Fe^{2+}$ ions.

5. The method for microbially dressing the super abrasive tool according to claim 4, wherein the binder comprises at least one kind of metal-based binder selected from the group consisting of copper-based, lead-based, zinc-based, cobalt-based, tin-based, chromium-based, cadmium-based, manganese-based, iron-based, nickel-based, and aluminum-based bond.

6. The method for microbially dressing the super abrasive tool according to claim 4, wherein culturing the microbes in step 2 comprises culturing the *Acidithiobacillus ferrooxidans* in a culture medium until the concentration of $Fe^{3+}$ ions is in the range of 6 g/L to 9 g/L to obtain the microbial culture liquid.

7. The method for microbially dressing the super abrasive tool according to claim 4, wherein in step 3, maintaining a temperature of the microbial culture liquid in a range of 25° C. to 45° C.

8. The method for microbially dressing the super abrasive tool according to claim 1, wherein the microbes comprise at least one of *Acidithiobacillus thiooxidans, Acidithiobacillus ferrooxidans, Acidithiobacillus caldus*, or *Leptospirillum ferrooxidans*.

9. The method for microbially dressing the super abrasive tool according to claim 1, wherein:
   when the at least one surface of the super abrasive tool to be dressed are immersed into the microbial culture liquid, rotating the super abrasive tool in the microbial culture liquid.

10. The method for microbially dressing the super abrasive tool according to claim 2, wherein the microbes comprise at least one of *Acidithiobacillus thiooxidans, Acidithiobacillus ferrooxidans, Acidithiobacillus caldus,* or *Leptospirillum ferrooxidans.*

\* \* \* \* \*